United States Patent [19]

Rooney et al.

[11] 4,181,661

[45] Jan. 1, 1980

[54] DERIVATIVES OF 2-IMINOTHIAZOLIDINES AND THIAZOLINES

[75] Inventors: Clarence S. Rooney, Worcester, Pa.; Joshua Rokach, Laval, Canada; Edward J. Cragoe, Jr., Lansdale, Pa.

[73] Assignee: Merck & Co., Inc., Rahway, N.J.

[21] Appl. No.: 875,270

[22] Filed: Feb. 6, 1978

Related U.S. Application Data

[63] Continuation-in-part of Ser. No. 773,232, Mar. 1, 1977, abandoned, which is a continuation-in-part of Ser. No. 682,876, May 3, 1976, abandoned.

[51] Int. Cl.$^2$ .................. A61K 31/435; C07D 417/12
[52] U.S. Cl. ..................... 548/195; 424/256; 424/270; 424/263; 546/116; 546/280

[58] Field of Search ............ 260/306.8 R; 546/280 R, 546/116

[56] References Cited

U.S. PATENT DOCUMENTS

| | | | |
|---|---|---|---|
| 3,671,650 | 6/1972 | Islip | 546/280 |
| 4,125,614 | 11/1978 | Lang et al. | 546/280 |

*Primary Examiner*—Glennon H. Hollrah
*Assistant Examiner*—J. H. Turnipseed
*Attorney, Agent, or Firm*—William H. Nicholson; Mario A. Monaco

[57] ABSTRACT

2-(Substituted imino)thiazolidines and thiazolines are inhibitors of indoleamine-N-methyl transferase in vivo. They are prepared by alkylation or acylation of the free imino group.

9 Claims, No Drawings

DERIVATIVES OF 2-IMINOTHIAZOLIDINES AND THIAZOLINES

BACKGROUND OF THE INVENTION

This is a continuation-in-part of U.S. application Ser. No. 773,232, filed Mar. 1, 1977, now abandoned which in turn is a continuation-in-part of U.S. application Ser. No. 682,876, filed May 3, 1976, now abandoned.

This invention is concerned with derivatives of 2-iminothiazolidine and of 2-iminothiazoline which by virtue of their ability to inhibit indoleamine-N-methyl transferase are useful in the treatment of certain mental aberrations in man, such as schizophrenia.

This invention also relates to processes for the preparation of the imines of this invention; to pharmaceutical compositions comprising the novel imines; and to a method of treating mental aberrations, such as schizophrenia, comprising the administration of the novel imines and compositions thereof. The novel imines may be depicted by the generic structure:

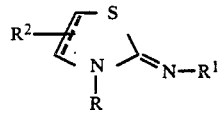

N,N-dimethylindoleamines such as dimethylserotonin and dimethyltryptamine are psychotomimetic agents and are believed to be produced in excessive amounts by individuals with certain mental aberrations, most commonly classified as schizophrenia. Indoleamine-N-methyl transferase is an enzyme which catalyzes the methylation steps in the bio-synthesis of these compounds. Accordingly, it is believed by those skilled in the art that inhibitors of this enzyme will be of therapeutic value in management of the body chemistry of patients having mental aberrations such as schizophrenia and thus result in alleviating some of the symptoms of the disease. Thus it is an object of the present invention to provide the above-described imines and their pharmaceutically acceptable salts; to provide processes for the preparation of such compounds; pharmaceutical compositions comprising such compounds; and to provide methods of treatment comprising administering such compounds and compositions, when indicated for the treatment/management of mental aberrations such as schizophrenia.

DETAILED DESCRIPTION OF THE INVENTION

The novel compounds of this invention have structural formula I:

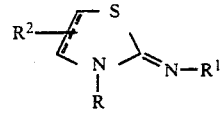

or pharmaceutically acceptable salt thereof, wherein R represents
(1) lower alkyl, especially $C_{1-3}$ alkyl, either straight or branched chain, such as methyl, ethyl, or propyl;
(2) $C_{3-5}$ alkenyl, such as allyl,
(3) lower alkynyl, especially $C_{3-5}$ alkynyl, such as propargyl;

R' represents
(1)

wherein $R^3$ represents
(a) lower alkyl, especially $C_{1-5}$ alkyl substituted with one or more groups selected from
  (i) amino,
  (ii) lower alkanoylamino, especially $C_{2-4}$-alkanoylamino,
  (iii) phenyl,
  (iv) carboxy,
  (v) lower alkanoyl, especially $C_{2-4}$ alkanoyl, or
  (vi) carboxamido, such as

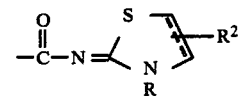

(b) pyridyl,
(2)

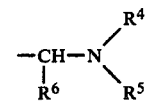

wherein
$R^6$ represents
  (a) hydrogen,
  (b) lower alkyl, especially $C_{1-5}$ alkyl,
  (c) phenyl, either unsubstituted or substituted with one or more lower alkoxy groups, especially $C_{1-3}$ alkoxy groups,
  (d) pyridyl;
$R^4$ represents
  (a) hydrogen, or
  (b) lower alkyl, especially $C_{1-3}$ alkyl, and
$R^5$ represents
  (a) lower alkyl, especially $C_{1-3}$ alkyl,
  (b) —$COR^7$, wherein $R^7$ represents
    (i) lower alkyl, especially $C_{1-3}$ alkyl,
    (ii) phenyl, or
$R^4$ and $R^5$ taken together, represent with the nitrogen to which they are attached

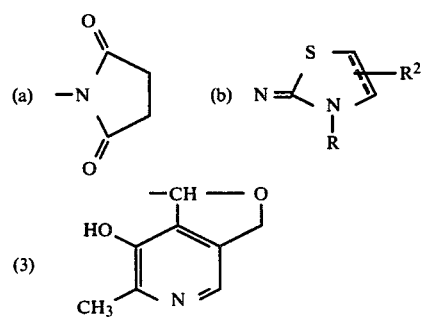

$R^2$ represents
(1) hydrogen, (2) lower alkyl, especially $C_{1-3}$ alkyl, or
(3) trifluoromethyl.

A preferred embodiment of the novel compounds is that wherein $R^1$ is —$COR^3$.

A still more preferred embodiment of the novel compounds is that wherein $R^1$ is —$COR^3$ and $R^3$ is pyridyl, lower alkanoylaminomethyl, lower alkanoylamino(benzyl)methyl, or 2-(3-methylthiazolidin-2-ylidenaminocarbonyl)ethyl.

The pharmaceutically acceptable salts contemplated by this invention are generally acid addition salts formed from a novel compound and an organic or inorganic acid recognized by the art as providing a pharmaceutically acceptable acid addition salt, such as hydrochloride, hydrobromide, dihydrogen phosphate, sulfate, citrate, pamoate, pyruvate, napsylate, isethionate, maleate, fumarate, or the like.

Where the novel compound has a free carboxylic acid group the pharmaceutically acceptable salt can be in the form of an ammonium, alkaline earth or alkali metal salt of the carboxylate group such as the sodium, potassium, calcium or the like salt.

A group of novel amide compounds is prepared in accordance with the following equation:

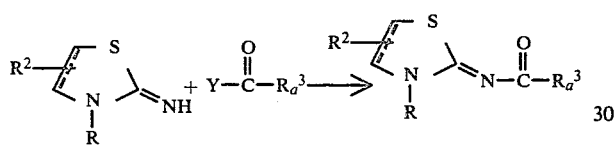

wherein Y is Cl—,

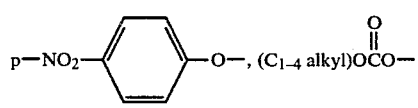

or $N_3$ and $R_a^3$ is aminolower alkyl, lower alkanoyl amino-lower alkyl, lower alkanoylamino-phenyl lower alkyl, pyridyl, lower alkanoyl-lower alkyl, or carboxamido-lower alkyl. Where $R_a^3$ is amino-lower alkyl, the reaction is conducted with the amino group protected such as with t-butoxycarbonyl. Where Y is

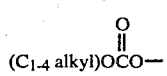

the acylating agent can be formed in situ by treating the corresponding free carboxylic acid group with a $C_{1-4}$ lower alkyl chloroformate. The reaction is conducted in an inert organic solvent such as a chlorinated hydrocarbon, for example, methylene chloride, chloroform, or dimethyl formamide at $-5°$ C. to $10°$ C. for 1–72 hours.

Where $R_a^3$ is carboxy-lower alkyl, the compounds are prepared by treating the 2-imino compound with a carboxylic anhydride such as succinic anhydride in a chlorinated hydrocarbon such as methylene chloride at $25°$ C. to reflux for 1–6 hours.

Where $R_a^3$ is acetylmethyl, it can also be prepared by treating the 2-imino compound with diketene at $0°$–$10°$ C. in a lower alkanol such as ethanol and allowing the mixture to warm to room temperature.

A second group of the novel compounds of this invention are prepared in accordance with the following equation:

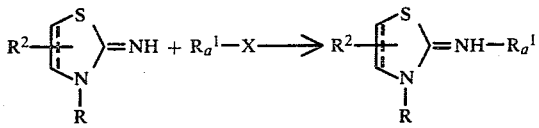

wherein X is Cl or —$N(CH_3)_2$ and $R_a^1$ is

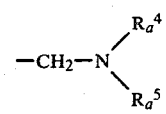

wherein
$R_a^4$ is hydrogen or lower alkyl,
$R_a^5$ is lower alkyl, or
—$COR^7$ wherein $R^7$ is lower alkyl or phenyl,
$R_a^4$ and $R_a^5$ taken together with the nitrogen to which they are attached is

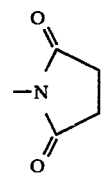

Where X is Cl the process is conducted by mixing the two starting materials at $0°$–$10°$ C. in an inert organic solvent, such as a chlorinated hydrocarbon, especially methylene chloride and warming to room temperature to $50°$ C. for up to about 6 hours. Where X is $(CH_3)_2N$—, the process is conducted by heating a mixture of the starting materials in an inert organic solvent, such as benzene, at $50°$ C. to reflux temperature for 10–24 hours.

Another group of novel compounds, that is, where $R^1$ is

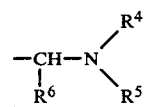

and $R^4$ and $R^5$ taken together with the nitrogen to which they are attached represent

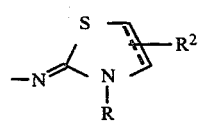

is prepared in accordance with the following equation:

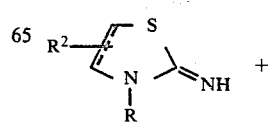

-continued

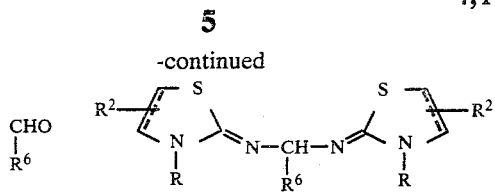

In the above equation, the reagent is indicated as an aldehyde for the sake of simplicity, but it is meant to include functional equivalents thereof, such as aldehyde precursors for example paraformaldehyde, aminals or the like. The process is conducted by mixing the starting material with the aldehyde or aldehyde precursor in an inert organic solvent such as benzene, toluene, or the like, and heating between 50° C. and reflux temperature with provision for removing water produced by the condensation reaction such as adding molecular sieves to the reaction mixture or refluxing in a Dean-Stark apparatus.

Under similar reaction conditions pyridoxal provides a compound of structure

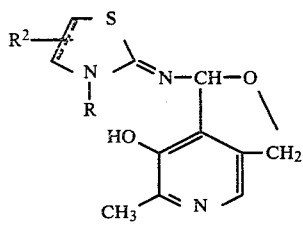

In the novel method of treatment of this invention the route of administration can be oral, rectal, intravenous, intramuscular, or intraperitoneal. Doses of 0.10 to 100 mg./kg./day and preferably of 1 to 10 mg./kg./day of active ingredient are generally adequate, and it is preferred that it be administered in divided doses given two to four times daily.

It is to be noted that the precise unit dosage form and dosage level depend upon the case history of the individual being treated and, consequently, are left to the discretion of a skilled therapist.

Pharmaceutical compositions comprising a compound useful in the novel method of treatments as active ingredient may be in any art recognized form suitable for oral use, such as tablets, troches, lozenges, aqueous or oil suspensions, dispersible powders, or granules, emulsions, hard or soft capsules, syrups, or elixirs. For intravenous and intramuscular and intraperitoneal use the pharmaceutical compositions may be in any art recognized form of a sterile injectable preparation such as a sterile aqueous or oleaginous solution or suspension. The amount of active ingredient incorporated in a unit dosage of the above described pharmaceutical compositions may be from 1 mg. to 500 mg.

EXAMPLE 1

3,5-Dimethyl-2-iminothiazolidine Fumarate

Step A: Preparation of methyl N-(2-hydroxypropyl)dithiocarbamate

40 G (0.242 mmole) of 1-amino-2-propanol oxalate was suspended in 180 ml. of pyridine and 101 g. of triethylamine was added. The mixture was stirred mechanically for 1 hour, there cooled to 0° and 38 g. of carbon disulfide (0.5 mole) was added dropwise. After 2 hours at 0° C., 36 g. of methyl iodide (0.254 mole) was added dropwise and almost all solids dissolved. The mixture was stored in a refrigerator overnight (0°–5° C.). The mixture was poured into 2.4 l. of 3 N $H_2SO_4$ and extracted with ether 3 times. The ether extracts were washed with water, 3 N $H_2SO_4$, water, aqueous $NaHCO_3$ solution and water, dried over $Na_2SO_4$ and stripped down to 18.79 g. (47%) of oily methyl N-(2-hydroxypropyl) dithiocarbamate.

Step B: Preparation of 5-methyl-2-methylthio-2-thiazoline 17.37 G. of the dithiocarbamate from Step A in 30 ml. dry ether was added to 73 ml. thionyl chloride at 0°–5° C. The mixture was stirred at 0° for 2 hours, then stored in a refrigerator overnight. The thionyl chloride was evaporated at 30° C. and the residual oil (containing elemental sulfur) was poured into saturated $NaHCO_3$ solution and extracted with ether. The etherial fraction was extracted with dilute HCl. The aqueous fraction was basified with NaOH solution and extracted with ether. Evaporation of the ether afforded 6.65 g. liquid residue. This was chromatographed on a column of silica gel using benzene as eluant to give 2.5 g. (16.2%) of oily 5-methyl-2-methylthio-2-thiazoline.

Step C: Preparation of 3,5-Dimethyl-2-methylthio-2-thiazoline fluoborate

588 Mg. of the S-methyl thiazoline from Step B and 592 mg. trimethyl oxonium fluoborate were stirred together in 40 ml. $CH_2Cl_2$ overnight at room temperature. The fluoborate dissolves slowly as it reacts. The reaction mixture was stripped to dryness to give a colorless oil which was used directly in the next step.

Step D: Preparation of 3,5-dimethyl-2-iminothiazolidine fumarate

The crude fluoborate salt from Step C was dissolved in 40 ml. of alcohol and the solution was saturated with gaseous $NH_3$. The solution was stirred at room temperature for 3 hours. The solution was evaporated to dryness The resulting oily residue was taken up in 10 ml. of water, then 40 ml. $CHCl_3$ was added with stirring and 40% NaOH solution was added to make the aqueous fraction strongly basic. The two layers were separated, and the aqueous fraction was extracted once more with $CHCl_3$. The combined $CHCl_3$ fraction was dried and concentrated to dryness to give 630 mg. of oil. The compound was converted to the fumarate, and crystallized from isopropanol-ether to give 720 mg. cream-colored crystals, m.p. 130°–138° C. (73%) overall. Recrystallization of the fumarate from isopropanol-ether gave 470 mg. 3,5-dimethyl-2-iminothiazolidine fumarate, m.p. 133°–6° C.

EXAMPLE 2

2-Imino-3-methyl-4-trifluoromethyl-4-thiazoline fluorosulfonate 336 mg. of 2-amino-4-trifluoromethylthiazole was dissolved in 15 mg. $CH_2Cl_2$. The flask was placed in an ice bath and 240 mg. of $CH_3SO_3F$ in 5 ml. $CH_2Cl_2$ was added. The mixture was then placed in a refrigerator over the weekend. The colorless crystals were collected on a filter to give 450 mg. (80%) of 2-imino-3-methyl-4-trifluoromethyl-4-thiazoline fluorosulfonate, m.p. 177°78° C.

EXAMPLE 3

2-Imino-3-methyl-4-thiazoline

A mixture of 1.0 g. of 2-aminothiazole and 2 ml. of methyliodide in 10 ml. of isopropanol was heated at reflux for 2 hours. The hot solution was treated with decolorizing carbon, filtered, and the filtrate was cooled in the refrigerator. The precipitate was collected on a filter, washed with isopropanol, and dried to give 1.377 g. (57%) of 2-imino-3-methyl-4-thiazoline.

EXAMPLE 4

2-Imino-3-methylthiazolidine.HCl.½ H₂O

A solution of 44.5 g. of the corresponding hydroiodide in 300 ml. of water was added to a suspension of 52.5 g. of silver chloride (0.366 mole) in 300 ml. of water. The mixture was stirred at 80° C. for 3½ hours, cooled and filtered. The filtrate was evaporated to dryness and the solid was crystallized from isopropanol and a little ether to give 23.73 g. (85%) of 2-imino-3-methylthiazolidine.HCl.½ H₂O, m.p. 73°-76° C.

Concentration of the mother liquors afforded a second crop of 4.17 g. of the product.

Employing the procedure substantially as described in Example 3, but substituting for the methyl iodide and the 2-aminothiazole used therein, an equimolecular amount of an organic halide of formula R-Hal and compound of formula:

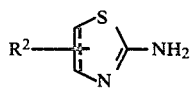

there are produced according to Equation I the 3-R-2 iminothiazolidines amd thiazolines identified in Table I.

Equation I

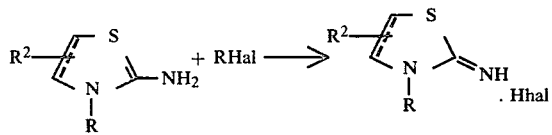

Table I

| R | R' | R² | Hal | m.p. (°C.) |
|---|---|---|---|---|
| Thiazolidines | | | | |
| CH₃CH₂CH₂— | H | H | Br | 121-123 |
| CH₃CH₂— | H | H | I | 80-83 (as maleate salt) |
| CH₂=CHCH₂ | H | H | Br | 112-116 |
| CH≡C—CH₂— | H | H | Br | 143-145 |
| Thiazolines | | | | |
| CH₃CH₂CH₂— | H | H | Br | — |
| CH₃CH₂— | H | H | I | — |
| CH₂=CHCH₂ | H | H | Br | — |
| CH≡C—CH₂— | H | H | Br | — |

EXAMPLE 5

2-Dimethylaminomethylimino-3-methylthiazolidine

A mixture of 600 mg. of 2-imino-3-methylthiazolidine, 10 mg. of its hydrogen iodide salt, and 550 mg. of bis(dimethylamino)methane in 10 ml. of benzene were refluxed overnight. The mixture was concentrated to dryness, and the residue was twice taken up in chloroform and evaporated to dryness to give 200 mg. of 2-dimethylaminomethylimino-3-methylthiazolidine, b.p. 98°-102° C. at 2.5 mm of Hg. pressure.

Following the procedure of Example 5, but substituting for the 2-imino-3-methylthiazolidine used therein, an equivalent amount of the 2-imino-3-R-thiazolidines and thiazolines depicted in Table II, there are produced the 2-dimethylaminomethylimino-3-R-thiazolidines and thiazolines also depicted in Table II, in accordance with Equation II:

Equation II

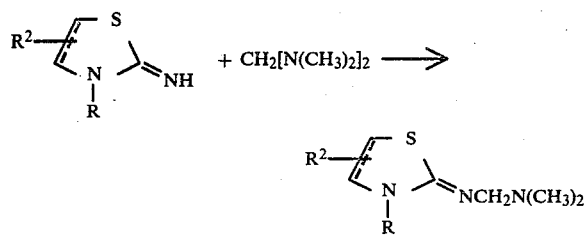

Table II

| R | R² |
|---|---|
| Thiazolines | |
| CH₃— | 4-CF₃ |
| CH₃— | H |
| Thiazolidines | |
| CH₃— | 5-CH₃ |
| C₂H₅— | H |
| C₃H₇— | H |
| CH₂=CH—CH₂— | H |

EXAMPLE 6

3-Methyl-2-Succinimidomethyliminothiazolidine

Bromomethylsuccinimide (53.9 g.) was added portion-wise to a mixture of 32.7 g. of 2-imino-3-methylthiazolidine and 42 ml. of triethylamine and 150 ml. of methylene chloride. A reaction occurred spontaneously. The mixture was evaporated to dryness, and the residue was taken up in chloroform and sodium hydroxide solution. The aqueous phase was separated and extracted three times with chloroform. The combined chloroform extracts were dried and concentrated to dryness. The residue was crystallized twice from benzene to give 13.5 g. of 3-methyl-2-succinimidomethyliminothiazolidine, m.p. 142°-144° C.

Following the procedure of Example 6, but substituting for the 2-imino-3-methylthiazolidine used therein, an equimolar amount of the 2-imino-3-R-thiazolidines and thiazolines depicted in Table III, there are produced the 2-succinimidomethylimino-3-R-thiazolidines and thiazolines also depicted in Table III, in accordance with Equation III.

Equation III

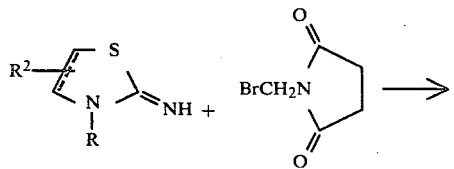

-continued
Equation III

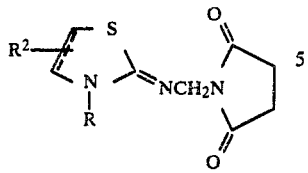

Table III

| R | R² |
|---|---|
| Thiazolines | |
| CH₃— | 4-CF₃ |
| CH₃— | H |
| Thiazolidines | |
| CH₃— | 5-CH₃— |
| C₂H₅— | H |
| C₃H₇— | H |
| CH₂=CH—CH₂— | H |
| CH≡C—CH₂— | H |

EXAMPLE 7

2-Benzamidomethylimino-3-methylthiazolidine, maleate

A solution of 676 mg. of N-chloromethyl benzamide in 15 ml. of methylene chloride was slowly added to an ice cold mixture of 2.0 ml. of triethylamine, 488 mg. of 2-imino-3-methylthiazolidine, and 25 ml. of methylene chloride. After stirring 2 hours at room temperature, the mixture was evaporated to dryness. The residue was dissolved in methylene chloride, washed with water, and dilute hydrochloric acid. The combined aqueous phases were basified with sodium bicarbonate and extracted with methylene chloride. The methylene chloride was washed with water, dried, and evaporated to dryness. The residue was triturated with ether and the product free base (250 mg.) was collected on a filter.

The maleate salt was prepared from 11.0 g. of free base and 5.12 g. of maleic acid in 100 m. methanol and isolated by adding ether to incipient cloudiness, seeding and cooling to give 10.42 g. of 2-benzamidomethylimino-3-methylthiazolidine, maleate, m.p. 120°–121° C.

A second crop of 4.28 g. was isolated from the mother liquors, m.p. 119°–120° C.

Employing the procedure substantially as described in Example 8, but substituting for the N-chloromethylbenzamide used therein, an equimolar amount of N-chloromethylpropionamide there is produced 2-propionamidomethylimino-3-methylthiazolidine and maleate salt thereof.

Following the procedure of Example 8, but substituting for the 2-imino-3-methylthiazolidine used therein, an equivalent amount of the 2-imino-3-R-thiazolidines and thiazolines depicted in Table IV, there are produced the 2-benzamidomethylimino-3-R-thiazolidines and thiazolines also depicted in Table IV, in accordance with Equation IV:

Equation IV

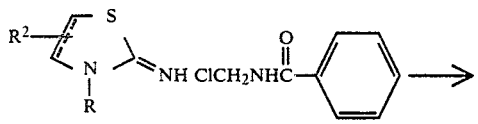

-continued
Equation IV

Table IV

| R | R² |
|---|---|
| Thiazolines | |
| CH₃— | 4-CF₃ |
| CH₃— | H |
| Thiazolidines | |
| CH₃— | 5-CH₃ |
| C₂H₅ | H |
| C₃H₇— | H |
| CH₂=CH—CH₂— | H |

EXAMPLE 8

Bis[3-methylthiazolidin-2-ylideneamino]methane

A mixture of 25 g. of 2-imino-3-methylthiazolidine, 6.5 g. of paraformaldehyde, 75 g. of molecular seives, and 250 ml. of benzene was refluxed for 5 hours. Molecular seives (30 g.) and 6.5 g. of paraformaldehyde were added and refluxing was continued overnight. The molecular seives were collected on a filter and washed well with benzene. The combined filtrate and washings were evaporated to dryness to give 21 g. of crystalline bis[3-methylthiazolidin-2-ylideneamino]methane, m.p 57°–59° C.

A hydrochloride salt was prepared by dissolving 350 mg. in 2 ml. of water and 2 ml. of 6 N hydrochloric acid and evaporating to an oily residue. Evaporation of acetone, isopropanol and benzene from the residue followed by trituration gave crystalline hydrochloride salt.

Employing the procedure substantially as described in Example 8 but substituting for the paraformaldehyde used therein an equimolar amount of acetaldehyde, benzaldehyde (or aminal), 3,4-dimethoxybenzaldehyde, 4-pyridinecarboxaldehyde and pyridoxal, there are produced respectively:

1,1-bis(3-methylthiazolidin-2-ylidenamino)ethane dihydrochloride, m.p. 292° C.

α,α-bis(3-methylthiazolidin-2-ylideneamino)toluene, m.p. 167°–169° C.;

α,α-bis(3-methylthiazolidin-2-ylideneamino)-3,4-dimethoxytoluene, m.p. 144°–145° C.

α,α-bis(3-methylthiazolidin-2-ylideneamino)-γ-picoline; m.p. 110°–113° C.

and

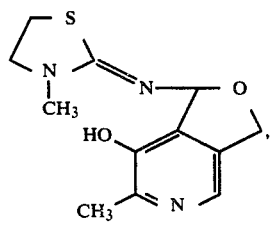

m.p. 172°–175° C.

Following the procedure of Example 8, but substituting for the 2-imino-3-methylthiazolidine and paraformaldehyde used therein, an equivalent amount of the 2-imino-3-R-thiazolidines and thiazolines and aldehydes depicted in Table V, there are produced the bis[3-R-thiazolidin-2-ylideneamino]-R³-methanes and bis[3-R-thiazolin-2-ylidineamino]-R³-methanes also depicted in Table V, in accordance with Equation V:

Equation V

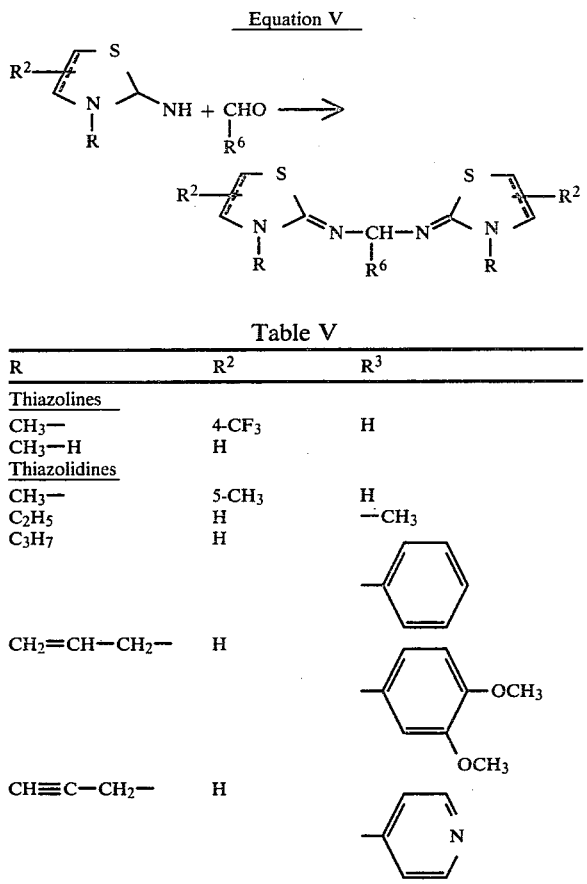

Table V

| R | R² | R³ |
|---|---|---|
| Thiazolines | | |
| CH₃— | 4-CF₃ | H |
| CH₃—H | H | |
| Thiazolidines | | |
| CH₃— | 5-CH₃ | H |
| C₂H₅ | H | —CH₃ |
| C₃H₇ | H | —⟨phenyl⟩ |
| CH₂=CH—CH₂— | H | —⟨dimethoxyphenyl, OCH₃, OCH₃⟩ |
| CH≡C—CH₂— | H | —⟨pyridyl, N⟩ | reagent is the aminal, N,N,N',N'-tetramethyltoluenediamine.

EXAMPLE 9

N,N'-bis-(3-methylthiazolidin-2-ylidene)succinamide

Step A: Preparation of bis-(4-nitrophenyl) succinate

A mixture of 2.36 g. (20 mmoles) of succinic acid, 6.516 g. (44 mmoles) of 4-nitrophenol and 8.24 g. (40 mmoles) of N,N'-dicyclohexylcarbodiimide was stirred at room temperature in 225 ml. of ethylacetate for 2 days. The mixture was filtered and the filtrate was concentrated to dryness. The residue was triturated with 40 ml. of chloroform and the solids were collected on a filter and air dried to give 1.38 g. of bis-(4-nitrophenyl) succinate, m.p. 176°–178° C.

Step B: Preparation of
N,N'-bis-(3-methylthiazolidin-2-ylidene)succinamide

A mixture of 80 mg. of 2-imino-3-methylthiazolidine, 118 mg. of bis-(4-nitrophenyl) succinate and 8 ml. of chloroform was refluxed for 5.5 hours. The mixture was diluted with chloroform, washed twice with sodium carbonate solution, dried over sodium sulfate and concentrated to dryness. The residue was recrystallized from 2 ml. of methanol to give 68 mg. of N,N'-bis-(3-methylthiazolidin-2-ylidene)succinamide, m.p. 181°–183° C.

EXAMPLE 10

N-(3-methylthiazolidin-2-ylidene) aminoacetamide dihydrochloride

Step A: Preparation of
N-(3-methylthiazolidin-2-ylidene)-t-butoxycarbonylaminoacetamide Ethyl chloroformate (0.25 ml.) at −5° C. was added to a solution of 350 mg. of t-butoxycarbonylaminoacetic acid and 0.4 ml. of triethylamine in 10 ml. of methylene chloride at −5° C. After stirring 5 minutes at −5° C. there was added a solution of 610 mg. of 2-imino-3-methylthiazolidine hydrogen iodide and 1.0 ml. of triethylamine in 10 ml. of methylene chloride also at −5° C. Stirring was continued at −5° C. for 15 minutes and one hour at room temperature. The reaction mixture was washed with 40 ml. of 20% (w/v) citric acid solution, sodium bicarbonate solution, and water, dried and concentrated to dryness. The residue was triturated with ether, petroleum ether and ether and finally collected to give pure N-(3-methylthiazolidin-2-ylidene)-t-butoxycarbonylaminoacetamide.

Step B: Preparation of
N-(3-methylthiazolidin-2-ylidene) aminoacetamide dihydrochloride The product from Step A, (2.0 g.) was dissolved in 100 ml. of chloroform and the solution was saturated with hydrogen chloride gas by bubbling it through the solution for 20 minutes. After 2 hours at room temperature the excess hydrogen chloride was expelled by bubbling in nitrogen. The precipitated product was collected and air dried under nitrogen to give 1.66 g. of N-(3-methylthiazolidin-2-ylidene) aminoacetamide dihydrochloride, m.p. 190°–194° C.

Employing the procedure substantially as described in Example 10, Step A, but substituting for the t-butoxycarbonylaminoacetic acid used therein an equimolar amount of 2-acetylamino-2-benzylacetic acid, nicotinic acid, acetoacetic acid and 3-methyl-2-succinyliminothiazolidine (See Example 11), there are produced respectively:

N-(3-methylthiazolidin-2-ylidene) 2-acetylamino-2-benzylacetamide, m.p. 142°–149° C.

N-(3-methylthiazolidin-2-ylidene) nicotinamide, m.p. 108°–109° C.

N-(3-methylthiazolidin-2-ylidene) acetoacetamide, m.p. 43°–45° C.; and

N,N'-bis-(3-methylthiazolidin-2-ylidene)succinamide, m.p. 183°–184° C.

Following the procedure of Example 10, but substituting for the 2-imino-3-methylthiazolidine used therein, an equivalent amount of the 2-imino-3-R-thiazolidines and thiazolines depicted in Table VIII, there are produced the N-(3-R-thiazolidin-2-ylidene)aminoacetamides and N-(3-R-thiazolin-2-ylidene)aminoacetamides also depicted in Table VI in accordance with Equation IV:

Equation VI

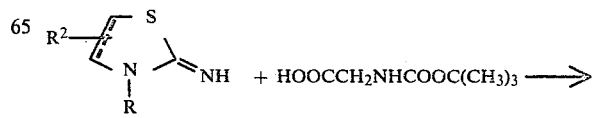

-continued
Equation VI

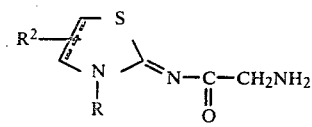

Table VI

| R | R² |
|---|---|
| Thiazolines | |
| CH₃— | 4-CF₃ |
| CH₃— | H |
| Thiazolidines | |
| CH₃ | 5-CH₃ |
| C₂H₅ | H |
| C₃H₇— | H |
| CH₂=CH—CH₂— | H |
| CH≡C—CH₂— | H |

EXAMPLE 11

N-(3-methylthiazolidin-2-ylidene) acetylaminoacetamide

4-Nitrophenyl acetylaminoacetate (1.19 g.) was added portionwise to a solution of 580 mg. of 2-imino-3-methylthiazolidine in 60 ml. of chloroform. After stirring 2 hours at room temperature, the solution was concentrated to dryness. The residue was triturated with ether and collected on a filter. The crude product was dissolved in chloroform, washed with sodium bicarbonate solution, dried and concentrated to dryness. Trituration with ether gave 600 mg. of N-(3-methyl-thiazolidin-2ylidene) acetylaminoacetamide, m.p. 138°–139° C.

Following the procedure of Example 11, but substituting for the 2-imino-3-methylthiazolidine used therein, an equivalent amount of the 2-imino-3-R-thiazolidines and thiazolines depicted in Table VII, there are produced the N-(3-R-thiazolidin-2-ylidene) acetylaminoacetamides and N-(3-R-thiazolin-2-ylidene) acetylaminoacetamides also depicted in Table IX, in accordance with Equation VII:

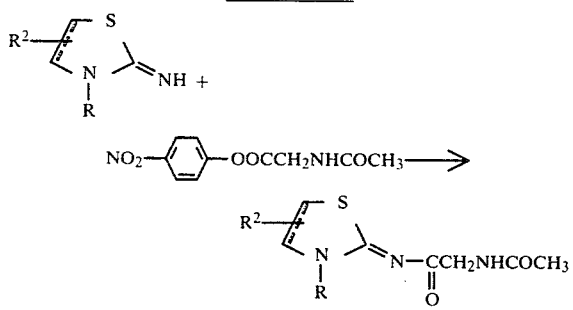

Equation VII

Table VII

| R | R² |
|---|---|
| Thiazolines | |
| CH₃— | 4-CF₃ |
| CH₃— | H |
| Thiazolidines | |
| CH₃— | 5-CH₃ |
| C₂H₅— | H |
| C₃H₇ | H |

Table VII-continued

| R | R² |
|---|---|
| CH₂=CH—CH₂— | H |
| CH≡C—CH₂— | H |

EXAMPLE 12

3-Methyl-2-succinyliminothiazolidine

Succinic anhydride (2.0 g.) was added to a solution of 2-imino-3-methylthiazolidine in 70 ml. of methylene chloride. After refluxing 3 hours, the mixture was filtered and the filtrate was evaporated to dryness. The residue was triturated with ether and collected on a filter to give 3.63 g. of 3-methyl-2-succinylimino-thiazolidine, m.p. 90°–105° C.

The product from Example 12 was converted to the sodium salt by dissolving 864 mg. of it in 25 ml. of water and adding 336 mg. of sodium bicarbonate. The mixture was concentrated to dryness and the residue was triturated with isopropanol. The solids were collected on a filter to give 730 mg. of 3-methyl-2-succinylimino-thiazolidine sodium salt, m.p. 205°–210° C.

Following the procedure of Example 12, but substituting for the 2-imino-3-methylthiazolidine used therein, an equivalent amount of the 2-imino-3-R-thiazolidines and thiazolines depicted in Table VIII, there are produced the 3-R-2-succinyliminothiazolidines and 3-R-2-succinyliminothiazolines also depicted in Table VIII, in accordance with Equation VIII:

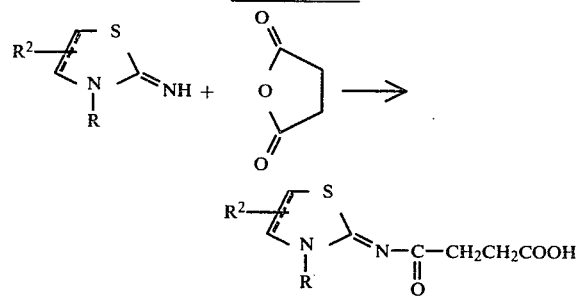

Equation VIII

Table VIII

| R | R² |
|---|---|
| Thiazolines | |
| CH₃— | 4-CF₃ |
| CH₃— | H |
| Thiazolidines | |
| CH₃— | 5-CH₃ |
| C₂H₅— | H |
| C₃H₇ | H |
| CH₂=CH—CH₂— | H |
| CH≡C—CH₂ | H |

EXAMPLE 13

2-Acetoacetylimino-3-methylthiazolidine

A solution of 13 g. of diketene in 100 ml. of ethanol was added dropwise to an ice-cold solution of 18 g. of 2-imino-3-methylthiazolidine in 100 ml. of ethanol. The mixture was allowed to warm spontaneously to room temperature and then evaporated to dryness. The residue was triturated with ether, collected on a filter and dried in a dessicator to give 2-acetoacetylimino-3-methylthiazolidine, m.p. 43°–45° C.

Following the procedure of Example 13, but substituting for the 2-imino-3-methylthiazolidine used therein, an equivalent amount of the 2-imino-3-R-thiazolidines and thiazolines depicted in Table IX, there are produced the 2-acetoacetylimino-3-R-thiazolidines and 2-acetoacetylimino-3-R-thiazolines also depicted in Table IX, in accordance with Equation IX:

Equation IX

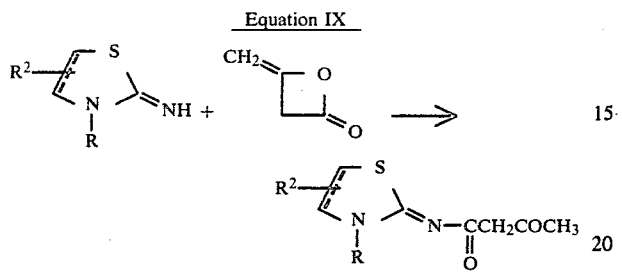

Table IX

| R | $R^2$ |
|---|---|
| Thiazolines | |
| $CH_3$— | 4-$CF_3$ |
| $CH_3$— | H |
| Thiazolidines | |
| $CH_3$— | 5-$CH_3$— |
| $C_2H_5$— | H |
| $C_3H_7$— | H |
| $CH_2$=CH—$CH_2$— | H |
| CH≡C—$CH_2$— | H |

EXAMPLE 14

Pharmaceutical Compositions

A typical tablet containing 5 mg. of N-(3-methylthiazolidin-2-ylidene) acetylaminoacetamide per tablet is prepared by mixing together with the active ingredient calcium phosphate, lactose and starch in the amounts shown in the tables below. After these ingredients are thoroughly mixed, the dry mixture blended for an additional three minutes. This mixture is then compressed into tablets weighing approximately 129 mg. each. Similarly prepared are tablets containing N-(3-methylthiazolidin-2-ylidene) 2-acetylamino-2-benzylacetamide; N-(3-methylthiazolidin-2-ylidene)-nicotinamide; and N,N'-bis-(3-methylthiazolidin-2-ylidene)succinamide.

| Tablet Formula | |
|---|---|
| Ingredient | Mg. per tablet |
| N-(3-methylthiazolidin-2-ylidene) acetylaminoacetamide | 5 mg. |
| Calcium phosphate | 52 mg. |
| Lactose | 60 mg. |
| Starch | 10 mg. |
| Magnesium stearate | 1 mg. |

| Tablet Formula | |
|---|---|
| Ingredient | Mg. Per Tablet |
| N-(3-methylthiazolidin-2-ylidene) 2-acetylamino-2-benzylacetamide | 5 mg. |
| Calcium phosphate | 52 mg. |
| Lactose | 60 mg. |
| Starch | 10 mg. |
| Magnesium stearate | 1 mg. |

| Tablet Formula | |
|---|---|
| Ingredient | Mg. per Tablet |
| N-(3-methylthiazolidin-2-ylidene)nicotinamide | 5 mg. |
| Calcium phosphate | 52 mg. |
| Lactose | 60 mg. |
| Starch | 10 mg. |
| Magnesium stearate | 1 mg. |

| Tablet Formula | |
|---|---|
| Ingredient | Mg. Per Tablet |
| N,N'-bis-(3-methylthiazolidin-2-ylidene)succinamide | 5 mg. |
| Calcium phosphate | 52 mg. |
| Lactose | 60 mg. |
| Starch | 10 mg. |
| Magnesium stearate | 1 mg. |

What is claimed is:
1. A compound of structural formula:

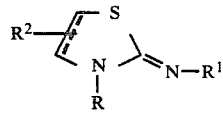

or pharmaceutically acceptable salt thereof, wherein
R is
 (1) $C_{1-3}$ alkyl,
 (2) $C_{3-5}$ alkenyl, or
 (3) $C_{3-5}$ alkynyl;
$R^1$ is
 (1)

wherein $R_3$ is
(a) $C_{1-5}$ alkyl, substituted with
 (i) amino,
 (ii) $C_{2-4}$ alkanoylamino,
 (iii) $C_{2-4}$ alkanoylamino and phenyl,
 (iv) carboxy,
 (v) $C_{2-4}$ alkanoyl, or
 (vi) [carboxamido]

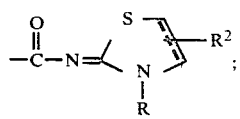

or
(b) pyridyl,
(2)

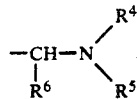

wherein
R⁶ is
  (a) hydrogen,
  (b) $C_{1-5}$ alkyl,
  (c) phenyl,
  (d) phenyl substituted with $C_{1-3}$ alkoxy,
  (e) pyridyl;
R⁴ is
  (a) hydrogen, or
  (b) $C_{1-3}$ alkyl; and
R⁵ is
  (a) $C_{1-3}$ alkyl,
  (b) —COR⁷, wherein R⁷ is
    (i) $C_{1-3}$ alkyl, or
    (ii) phenyl; or
R⁴ and R⁵ taken together with the nitrogen to which they are attached is (a) 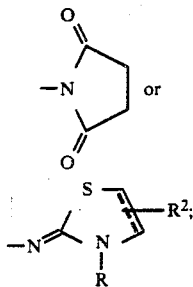 or (b) 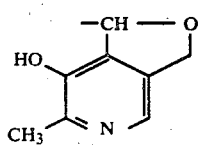

(3) 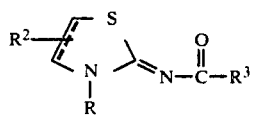

R² is
  (1) hydrogen,
  (2) $C_{1-3}$ alkyl, or
  (3) trifluoromethyl.

2. A compound of structural formula:

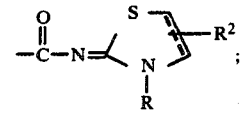

or pharmaceutically acceptable salt thereof, wherein
R is
  (1) $C_{1-3}$ alkyl,
  (2) $C_{3-5}$ alkenyl, or
  (3) $C_{3-5}$ alkynyl;
R² is
  (1) hydrogen,
  (2) $C_{1-3}$ alkyl, or
  (3) trifluoromethyl;
R³ is
  (1) substituted with
    (i) amino,
    (ii) $C_{2-4}$ alkanoylamino,
    (iii) $C_{2-4}$ alkanoylamino and phenyl,
    (iv) carboxy,
    (v) $C_{2-4}$ alkanoyl, or
    (vi) [carboxamido]

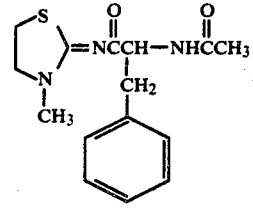

or
  (2) pyridyl.

3. The compound of structural formula:

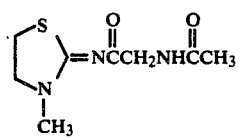

or pharmaceutically acceptable salt thereof.

4. The compound of structural formula:

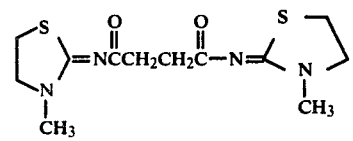

or pharmaceutically acceptable salt thereof.

5. The compound of structural formula:

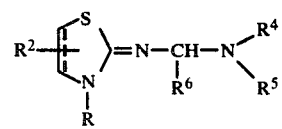

or pharmaceutically acceptable salt thereof.

6. A compound of structural formula:

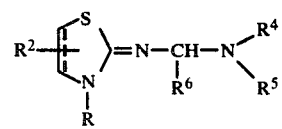

or a pharmaceutically acceptable salt thereof, wherein
R is
  (1) $C_{1-3}$ alkyl,
  (2) $C_{3-5}$ alkenyl, or
  (3) $C_{3-5}$ alkynyl;
R⁶ is
  (1) hydrogen,
  (2) $C_{1-5}$ alkyl,
  (3) phenyl,
  (4) phenyl substituted with $C_{1-3}$ alkoxy,
  (5) pyridyl;
R⁴ is (1) hydrogen, or
(2) $C_{1-3}$ alkyl; and $R^5$ is
(1) $C_{1-3}$ alkyl,
(2) —$COR^7$, wherein $R^7$ is
 (i) $C_{1-3}$ alkyl, or
 (ii) phenyl; or $R^4$ and $R^5$ taken together with the nitrogen to which they are attached is

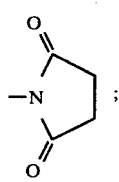

and
$R^2$ is
(1) hydrogen,
(2) $C_{1-3}$ alkyl, or
(3) trifluoromethyl.

7. A compound of structural formula:

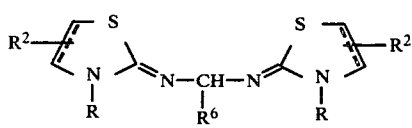

or pharmaceutically acceptable salt thereof, wherein
R is
(1) $C_{1-3}$ alkyl,
(2) $C_{3-5}$ alkenyl, or
(3) $C_{3-5}$ alkynyl;
$R^2$ is
(1) hydrogen,
(2) $C_{1-3}$ alkyl, or
(3) trifluoromethyl; and
$R^6$ is
(1) hydrogen,
(2) $C_{1-5}$ alkyl,
(3) phenyl,
(4) phenyl substituted with $C_{1-3}$ alkoxy or
(5) pyridyl.

8. A compound of structural formula:

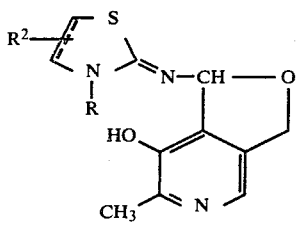

or pharmaceutically acceptable salt thereof, wherein
R is
(1) $C_{1-3}$ alkyl,
(2) $C_{3-5}$ alkenyl, or
(3) $C_{3-5}$ alkynyl; and
$R^2$ is
(1) hydrogen,
(2) $C_{1-3}$ alkyl, or
(3) trifluoromethyl.

9. A compound of formula:

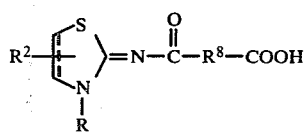

or pharmaceutically acceptable salt thereof, wherein
R is
(1) $C_{1-3}$ alkyl,
(2) $C_{3-5}$ alkenyl, or
(3) $C_{3-5}$ alkynyl;
$R^2$ is
(1) hydrogen;
(2) $C_{1-3}$ alkyl, or
(3) trifluoromethyl; and
$R^8$ is $C_{1-5}$ alkylene.

* * * * *

UNITED STATES PATENT AND TRADEMARK OFFICE
CERTIFICATE OF CORRECTION

PATENT NO. : 4,181,661

DATED : Jan. 1, 1980

INVENTOR(S) : CLARENCE S. ROONEY ET AL.

It is certified that error appears in the above-identified patent and that said Letters Patent are hereby corrected as shown below:

Column 16, line 58 delete, "[carboxamido]".

Column 18, line 1 should read --- (1) $C_{1-5}$ alkyl substituted with ---

Signed and Sealed this

Eighth Day of April 1980

[SEAL]

Attest:

SIDNEY A. DIAMOND

Attesting Officer

Commissioner of Patents and Trademarks